United States Patent [19]

Folz et al.

[11] Patent Number: 5,498,798
[45] Date of Patent: Mar. 12, 1996

[54] 4-ALKYL-3-CHLOROBENZENESULFINIC ACIDS, 4-ALKYL-3-CHLOROBENZENESULFONYLCARBOXYLIC ACIDS, 4-ALKYL-3-CHLOROALKYLSULFONYLBENZENES AND PREPARATION THEREOF

[75] Inventors: Georg Folz; Theodor Papenfuhs, both of Frankfurt am Main, Germany

[73] Assignee: Hoechst AG, Germany

[21] Appl. No.: 220,791

[22] Filed: Mar. 31, 1994

[30] Foreign Application Priority Data

Apr. 3, 1993 [DE] Germany ............. 43 11 079.7

[51] Int. Cl.$^6$ ................................................. C07C 315/04
[52] U.S. Cl. ...................... 568/28; 560/17; 562/429
[58] Field of Search ..................... 560/17, 429; 568/23

[56] References Cited

U.S. PATENT DOCUMENTS 4,675,447  6/1987  Ludvik ........................... 568/37

FOREIGN PATENT DOCUMENTS

| 260493 | 9/1988 | Germany | 568/33 |
| 43036 | 3/1987 | Hungary | 568/27 |
| 90/06301 | 6/1990 | WIPO | 568/27 |
| 91/07384 | 5/1991 | WIPO | 568/23 |
| 92/14700 | 9/1992 | WIPO | 568/23 |

OTHER PUBLICATIONS

Müller, E., *Houben–Weyl*, "Methoden der Organischen Chemie", vol. 5, Stuttgart, Germany Georg Thieme Verlag, 1962, p. 715. (Halogen Compounds).
*Ullmanns Encyklopadie der technischen Chemie*, Fourth Ed., vol. 8, 1974, p. 422.
Helvitica Chimica Acta, Bd. 66, Nr. 104, 1983 pp. 1046–1052, (Jun. 1983).
Chemical Abstracts, vol. 119, No. 1, 1993 Abstract No. 8503n, (Feb. 1973).

*Primary Examiner*—James H. Reamer
*Attorney, Agent, or Firm*—Connolly & Hutz

[57] ABSTRACT

Process for preparing 4-alkyl-3-chloroalkylsulfonylbenzenes of the formula (1)

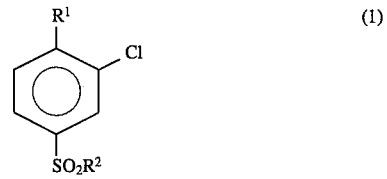

(1)

in which $R^1$ and $R^2$ are identical or different and are each $(C_1–C_4)$-alkyl.

18 Claims, No Drawings

4-ALKYL-3-CHLOROBENZENESULFINIC ACIDS, 4-ALKYL-3-CHLOROBENZENESULFONYLCARBOXYLIC ACIDS, 4-ALKYL-3-CHLOROALKYLSULFONYLBENZENES AND PREPARATION THEREOF

DESCRIPTION

4-Alkyl-3-chlorobenzenesulfinic acids, 4-alkyl-3-chlorobenzenesulfonylcarboxylic acids, 4-alkyl-3-chloroalkylsulfonylbenzenes and preparation thereof.

The invention relates to 4-alkyl-3-chlorobenzenesulphinic acids, 4-alkyl-3-chlorobenzenesulfonylcarboxylic acids, 4-alkyl-3-chloroalkylsulfonylbenzenes and processes for the preparation thereof.

According to U.S. Pat. No. 4,675,447, the reaction of 4-alkyl-alkylsulfonylbenzenes with sulfuryl chloride in the presence of a catalyst leads to 4-alkyl-3-chloroalkylsulfonylbenzenes. However, starting with 4-methyl-methylsulfonylbenzene, only the preparation of 4-methyl-3-chloromethylsulfonylbenzene and hence only the existence of this compound are documented. U.S. Pat. No. 4,675,447 makes no reference to the 4-alkyl-alkylsulfonylbenzenes required for the preparation of 4-alkyl-3-chloroalkylsulfonylbenzenes —save 4-methyl-methylsulfonylbenzene. A disadvantage of this process is the use of the expensive sulfuryl chloride which unavoidably leads to the formation of a considerable amount of polluting sulfur dioxide. In addition, the process requires the provision of a very dry starting material. A further disadvantage is that U.S. Pat. No. 4,657,447 does not disclose how the 4-alkyl-alkylsulfonylbenzenes to be used as starting material are to be obtained.

It is an object of the present invention to develop a process which avoids the abovementioned disadvantages and, first, starts from readily available starting materials and, secondly, has minimal environmental impact and in addition makes it possible to introduce the alkyl groups into the product as required.

This object is achieved by a process for preparing 4-alkyl-3-chloroalkylsulfonylbenzenes of the formula (1)

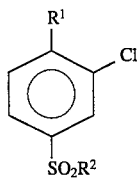

in which $R^1$ and $R^2$ are identical or different and are each $(C_1-C_4)$-alkyl. It comprises chlorinating a p-alkylbenzenesulfonyl chloride of the formula (2)

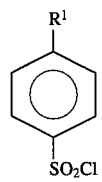

in which $R^1$ is as defined above, with at least 1 mol of chlorine in the presence of a catalyst at temperatures from about 50° to about 100° C. to form a compound of the formula (3)

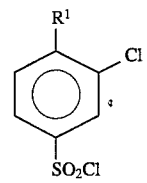

in which $R^1$ is as defined above, subsequently reducing this compound in aqueous medium with sodium sulfite or bisulfite at temperatures from about 40° to about 90° C. to a compound of the formula (4)

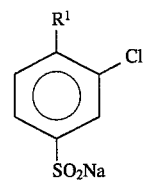

in which $R^1$ is as defined above, condensing this compound with an α-halocarboxylic acid of the formula (5)

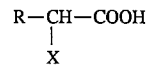

in which R is hydrogen or $(C_1-C_3)$-alkyl and X is bromine or chlorine, or a salt thereof, to form 4-alkyl-3-chloro-4-benzenesulfonylcarboxylic acids of the formula (6), in which $R^1$ and R are as defined above, or a salt thereof

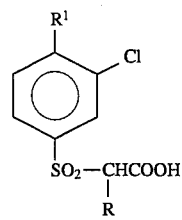

and subsequently decarboxylating these by heating.

The compounds of the invention which can be obtained by the process of the invention are compounds of the formula (1) in which $R^1$ is $(C_1-C_4)$-alkyl and $R^2$ is $(C_2-C_4)$-alkyl or $R^1$ is $(C_2-C_4)$-alkyl and $R^2$ is $(C_1-C_4)$-alkyl and also compounds of the formula (4) in which $R^1$ is $(C_1-C_4)$-alkyl and compounds of the formula (6) in which R is hydrogen or $(C_1-C_3)$-alkyl and $R^1$ is $(C_1-C_4)$-alkyl and alkali metal salts thereof.

Preference is here given to compounds of the formula (1) in which $R^1$ is methyl or ethyl and $R^2$ is ethyl, propyl or butyl, in particular each is ethyl. These compounds are useful starting materials for herbicides, insecticides and pharmaceuticals.

The process starts from 4-alkylbenzenesulfonyl chlorides which can be obtained by known methods (Ullmanns Encyclopädie der technischen Chemie, Volume 8, 4th edition, p. 422) from alkyl$(C_1-C_4)$benzenes and sulfuric acid with subsequent chlorination. The chlorination of the 4-alkylbenzenesulfonyl chlorides is advantageously carried out in the absence of solvents by passing in chlorine at temperatures from about 50° C. to about 100° C. in the presence of a chlorine carrier as catalyst.

In many cases, chlorination temperatures from 60° to 90° C., preferably from 70° to 80° C., have proven useful. An advantageous catalyst (chlorine transferrer) is iron(III) chloride or iron(III) chloride and iodine. However, catalysts which can also be used are, for example, $SbCl_3$ or $SbCl_5$. The chlorination is stopped at a degree of chlorination of about 100% (end-point determination by gas chromatography). Besides traces of the starting compound, the product contains only very small amounts of the dichloro compound. It can be used for further processing without purification, but can also be washed, and distilled and fractionated. The yield of 4-alkyl($C_1$–$C_4$)- 3-chlorobenzenesulfonyl chlorides is virtually quantitative.

The reduction of the 4-alkyl ($C_1$–$C_4$)- 3-chlorobenzenesulfonyl chlorides to the 4-alkyl ($C_1$–$C_4$)- 3-chlorobenzenesulfinic acids can be carried out with sodium sulfite or bisulfite (cf. Houben-Weyl, Vol. 9, pp. 305–311).

The reduction is advantageously carried out in aqueous medium by initially charging a solution of sodium sulfite or bisulfite and simultaneously adding 4-alkyl-3-chlorobenzenesulfonyl chloride and 35% strength sodium hydroxide solution dropwise while monitoring the pH and maintaining it at from 8 to 10.

The sulfonyl chloride can also be added to the sulfite solution and the sodium hydroxide solution added while maintaining a pH from about 8 to about 10. The concentration of the sulfite solution can lie between about 10 and about 30%, an about 15% strength solution being preferable. The amount of sulfite is from I to 1.2 mol, in particular from 1.08 to 1.15 mol. The reaction proceeds at a temperature from 40° to 90° C., preferably between 50° and 65° C. The reduction is complete when the pH from 8 to 10 remains constant. The sodium salt of 4-alkyl ($C_1$–$C_4$)- 3-chlorobenzenesulfinic acid crystallizes out of the solution at about 45° C. The compound can, without intermediate isolation, be processed further in the same apparatus, i.e. as part of a single-vessel process.

The salts of 4-alkyl-3-chlorobenzenesulfinic acids obtained are alkylated to the 4-alkyl-3-chlorobenzenesulfonylcarboxylic acids by metered addition of the corresponding 2-halocarboxylic acids of the formula (5) or salts thereof (Na, K, ammonium) to the sulfinic acids (Na salts) at from 40° to 60° C. over a period of from 10 minutes to 2 hours, preferably over 0.5 hours, in an amount from 1 to 1.5 mol, preferably from 1.1 to 1.3 mol. If the free carboxylic acids are added, these are converted into the salts by "neutralization" with the corresponding bases (e.g. sodium hydroxide solution 35% strength). To complete the condensation, the mixture is stirred further for about 2 to 3 hours at 60° C. (significantly above 60° C., losses in yield caused by increased hydrolysis of the halocarboxylic acid are likely. The arylsulfonylcarboxylic acid derivative formed in the reaction can be isolated, but can also be decarboxylated without isolation by heating the reaction solution to, preferably, from 90° to 110° C. (reflux) until $CO_2$ is no longer evolved; the time required is from 6 to 12 hours. The product can be obtained by crystallization and filtration, liquid/liquid separation (temperature above the melting point) and extraction (e.g. with toluene, chlorobenzene, etc).

The following examples serve to illustrate the process of the invention, without limiting it to them.

EXAMPLE I (CHLORINATION)

Preparation of 3-chloro-4-methylbenzenesulfonyl chloride 576 g (3 mol) of 4-methylbenzenesulfonyl chloride are melted in a chlorination apparatus. After addition of 7 g of iron(III) chloride and 2 g of iodine, elemental chlorine is passed in (5 l $Cl_2$/h) at from 75° to 80° C. until 100% chlorination is achieved (GC analysis).

The product can, after removal of residual chlorine and HCl, be used in crude form; but it can also be washed and, if desired, distilled.

The yield is about 100% of theory. Purity≧97% (besides small amounts of starting compound and dichloro compound).

EXAMPLE 2

Preparation of 3-chloro-4-methyl-methylsulfonylbenzene via the sodium salts of 3-chloro-4-methylbenzenesulfinic acid (a) and 3-chloro-4-methylbenzenesulfonylacetic acid (b)

(a) Reduction 1800 ml of water and 420 g (3.3 mol) of sodium sulfite are charged into a stirred apparatus fitted with 2 dropping funnels and a pH electrode and heated to from 50° to 55° C. Over a period of about 2 hours, 677 g (3 mol) of 3-chloro- 4-methylbenzenesulfonyl chloride and at the same time 690 g of NaOH, 35% strength, are allowed to run in in such a way that a pH from 8 to 10 is always maintained. The temperature may be allowed to rise to 65° C. The reaction is complete when the pH from 8 to 10 remains constant. The 3-chloro-4-methylbenzenesulfinic acid (Na salt) produced is dissolved at 65° C. and partially crystallizes out from about 55° C.

(b) Alkylation

The conversion of the sulfinate formed according to (a) to the methylsulfone is carried out in the same apparatus. For this purpose, the solution or suspension obtained in (a) is admixed at from 50° to 60° C. with 331 g (3.5 mol) of chloroacetic acid over a period of about 30 minutes. The pH is adjusted to from 9 to 10 with 377 g of sodium hydroxide solution, 35% strength, (3.3 mol) (formation of the sodium salt of chloroacetic acid) and to complete the condensation (formation of the sodium salt of 3-chloro-4-methylbenzenesulfonylacetic acid) the mixture is stirred for from 2 to 3 hours at 60° C. It is then heated to from 95° to 105° C. (reflux). The carboxylation commences gradually at about 90° C. and is continued by heating for from 6 to 8 hours until $CO_2$ is no longer evolved. The initially clear solution changes, at the rate at which the sulfone is formed, into an emulsion from which on cooling the product (3-chloro-4-methyl-methylsulfonylbenzene) is separated out in crystalline form and filtered off.

The yield is about 90%; purity:≧97%; melting point from 89° to 91° C.

EXAMPLE 3

Preparation of 3-chloro-4-methyl-ethylsulfonylbenzene via the sodium salts of 3-chloro-4-methylbenzenesulfinic acid (a) and 3-chloro-4-methylbenzenesulfonylpropionic acid (b)

380 g (3.5 mol) of 2-chloropropionic acid are metered into a solution or suspension of 3-chloro-4-methylbenzenesulfinate prepared in accordance with Example 2 (a) in the same apparatus at from 50 to 60° C. over a period of about 30 minutes. The pH is adjusted to from 9 to 10 with 380 g of sodium hydroxide solution, 35% strength, (3.3 mol) (formation of the sodium salt of chloropropionic acid) and to complete the condensation (formation of the sodium salt of 3-chloro-4-methylbenzenesulfonylpropionic acid) the mixture is stirred for from 2 to 3 hours at 60° C. It is then heated up to from 95° to 105° C. (reflux). Decarboxylation commences gradually at about 90° C. and is continued until $CO_2$ is no longer evolved. The mixture is crystallized by cooling and the product is isolated by filtration.

The yield is about 90% of theory, purity: ≧97%; melting point: from 50° to 52° C.

$C_9H_{11}ClO_2S$: calc.: C 49.38%; H 5.029%; Cl 16.23 found: C 49.19%; H 5.014%; Cl 16.37%

EXAMPLE 4 (CHLORINATION)

Preparation of 3-chloro-4-ethylbenzenesulfonyl chloride

The procedure described in Example 1 is repeated, except that 615 g (3 mol) of 4-ethylbenzenesulfonyl chloride (prepared by, for example, reaction of 4-ethylbenzenesulfonic acid with chlorosulfuric acid) are used. The yield is about 100% of theory. Purity:≧96% (besides a small amount of starting compound and dichloro compound)

Solidification point: from 21° to 22° C. Boiling point (2.5 to 3 mm of Hg): from 129° to 130° C. $C_8H_8Cl_2O_2S$: calc.: C 40.18%; H 3.37%; Cl 29.65% found: C 40.02%; H 3.29%; Cl 29.73

EXAMPLE 5

Preparation of 3-chloro-4-ethyl-methylsulfonylbenzene via the sodium salts of 3-chloro-4-ethylbenzenesulfinic acid (a) and 3-chloro-4-ethylbenzenesulfonylacetic acid (b)

(a) Reduction

The procedure described in Example 2 (a) is repeated, except that 718 g (3 mol) of 3-chloro- 4-ethylbenzenesulfonyl chloride are used. The sodium salt of 3-chloro-4-ethylbenzenesulfinic acid does not crystallize until a lower temperature is reached.

(b) Alkylation

The conversion of the sulfinate formed to the methyl sulfone is carried out in the same apparatus as in Example 2 (b) via the sodium salt of 3-chloro- 4-ethylbenzenesulfonylacetic acid.

The yield is about 88% of theory Purity:≧96%; melting point: from 58° to 60° C. $C_9H_{11}ClO_2S$: calc.: C 49.427%; H 5.07%; Cl 16.21% found: C 49.29%; H 5.03%; Cl 16.32%

EXAMPLE 6

Preparation of 3-chloro-4-ethyl-ethylsulfonylbenzene via the sodium salts of 3-chloro-4-ethylbenzenesulfinic acid (a) and 3-chloro-4-ethylbenzenesulfonylpropionic acid (b)

The reaction of a solution or suspension of 3-chloro-4-ethylbenzenesulfinate (a) prepared in accordance with Example 5 (a) with 2-chloropropionic acid to form the sodium salt of 3-chloro-4-ethylbenzenesulfonylpropionic acid (b) and the decarboxylation are carried out by the procedure of Example 3. All steps are carried out in the same apparatus (single-vessel process).

The yield is about 80% of theory Purity:≧96%; melting point: from 36° to 37° C. $C_{10}H_{13}ClO_2S$: calc.: C 51.609%; H 5.633%; Cl 15.233% found: C 51.53%; H 5.49%; Cl 15.37%

What is claimed is:

1. A process for preparing 4-alkyl-3-chloroalkylsulfonylbenzenes of the formula (1)

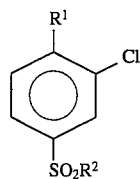

in which $R^1$ and $R^2$ are identical or different and are each ($C_1$–$C_4$)-alkyl, which comprises chlorinating a p-alkylbenzenesulfonyl chloride of the formula (2)

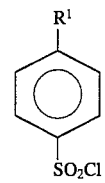

in which $R^1$ is as defined above, with at least 1 mol of chlorine per mole of said chloride of the formula (2) in the presence of a chlorine transferrer at a temperature ranging from about 50° to about 100° C. to form a compound of the formula (3)

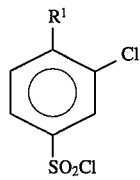

in which $R^1$ is as defined above, subsequently reducing this compound in aqueous medium with sodium sulfite or bisulfite at a temperature ranging from about 40° to about 90° C. to a compound of the formula (4)

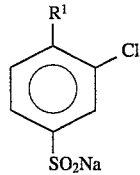

in which $R^1$ is as defined above, condensing this compound with an α-halocarboxylic acid of the formula (5)

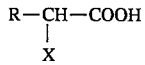

in which R is hydrogen or ($C_1$–$C_3$)-alkyl and X is bromine or chlorine, or a salt thereof, to form a 4-alkyl-3-chlorobenzenesulfonylcarboxylic acid of the formula (6), in which $R^1$ and R are as defined above, or a salt thereof

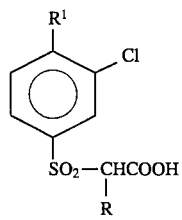

and subsequently decarboxylating it by heating.

2. The process as claimed in claim 1, wherein the chlorinating step is carried out at a temperature ranging from 60° to 90° C.

3. The process as claimed in claim 2, wherein said temperature ranges from 70° to 80° C.

4. The process as claimed in claim 1, wherein said chlorine transferrer comprises iron(III) chloride.

5. The process as claimed in claim 4, wherein said chlorine transferrer comprises iron(III) chloride and iodine.

6. The process as claimed in claim 1, wherein said reducing step is carried out at a temperature ranging from 40° to 90° C. and at a pH ranging from 8 to 10.

7. The process as claimed in claim 6, wherein said temperature ranges from 50° to 65° C.

8. The process as claimed in claim 6, wherein the amount of sodium sulfite or bisulfite ranges from 1 to 1.2 mol per mol of said compound of the formula (3).

9. The process as claimed in claim 8, wherein said amount ranges from 1.08 to 1.15 mol per mole of said compound of the formula (3).

10. The process as claimed in claim 1, wherein said condensing step is carried out with an amount of said α-halocarboxylic acid or salt thereof ranging from 1 to 1.5 mol per mol of said compound of the formula (4).

11. The process as claimed in claim 10, wherein said amount of said α-halocarboxylic acid or salt thereof ranges from 1.1 to 1.30 mol per mol of said compound of the formula (4).

12. The process as claimed in claim 11, wherein said α-halocarboxylic acid is an α-chlorocarboxylic acid.

13. The process as claimed in claim 1, wherein said condensing step is carried out at a temperature ranging from 40° to 70° C.

14. The process as claimed in claim 13, wherein said temperature ranges from 50° to 60° C.

15. The process as claimed in claim 1, wherein at least one of the intermediate products resulting from said chlorinating, reducing, or condensing steps is isolated during the process.

16. The process as claimed in claim 1, wherein none of the intermediate products resulting from said chlorinating, reducing, or condensing steps is isolated during the process, but a said 4-alkyl-chloralkylsulfonylbenzene is isolated after said heating step.

17. The process as claimed in claim 10, wherein said condensing step is carried out at a temperature ranging from 40° to 70° C.

18. The process as claimed in claim 17, wherein said condensing step is carried out at a temperature ranging from 50° to 60° C., said reducing step is carried out at a temperature ranging from 50° to 65° C. and a pH ranging from 8 to 10, and said chlorinating step is carried out at a temperature ranging from 70° to 80° C.

* * * * *